United States Patent [19]

Gerdau et al.

[11] Patent Number: 4,859,795
[45] Date of Patent: Aug. 22, 1989

[54] ETHYLENICALLY UNSATURATED PHOSPHINIC ACID AND THIOPHOSPHINIC ACID ISOCYANATES AND ISOTHIOCYANATES, AND A PROCESS FOR THEIR PREPARATION

[75] Inventors: Thomas Gerdau, Eppstein; Hans-Jerg Kleiner, Kronberg; Georg Pawlowski, Wiesbaden, all of Fed. Rep. of Germany

[73] Assignee: Hoechst Aktiengesellschaft, Fed. Rep. of Germany

[21] Appl. No.: 47,102

[22] Filed: May 8, 1987

[30] Foreign Application Priority Data

May 9, 1986 [DE] Fed. Rep. of Germany ....... 3615614

[51] Int. Cl.⁴ ................................................ C07F 9/53
[52] U.S. Cl. ...................................................... 564/12
[58] Field of Search ........................................... 564/12

[56] References Cited

U.S. PATENT DOCUMENTS 3,048,631  8/1962  Audrieth et al. .................... 564/12
3,621,083  11/1971  Price .................................. 260/545 P

FOREIGN PATENT DOCUMENTS 3615612 11/1987 Fed. Rep. of Germany .

Primary Examiner—Anton H. Sutto
Attorney, Agent, or Firm—Foley & Lardner, Schwartz,Jeffery,Schwaab,Mack,Blumenthal,& Evans

[57] ABSTRACT

Compounds of the general formula

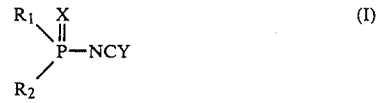

wherein
X and Y are the same or different and denote oxygen or sulfur,
$R_1$ is an ethylenically unsaturated aliphatic radical containing from 2 to 6 carbon atoms, and
$R_2$ is a saturated aliphatic radical containing from 1 to 6 carbon atoms or an aryl radical containing from 6 to 10 carbon atoms, are intermediate products used for the preparation of photocrosslinkable polymers with lateral (thio)phosphinyl(thio)urethane groups or (thio)phosphinyl(thio)urea groups, which polymers are useful in photosensitive mixtures and recording material.

10 Claims, No Drawings

ETHYLENICALLY UNSATURATED PHOSPHINIC ACID AND THIOPHOSPHINIC ACID ISOCYANATES AND ISOTHIOCYANATES, AND A PROCESS FOR THEIR PREPARATION

BACKGROUND OF THE INVENTION

The present invention relates to ethylenically unsaturated phosphinic acid and thiophosphinic acid isocyanates and isothiocyanates, and to a process for their preparation. These compounds can be used as starting products for the preparation of photocrosslinkable polymers which are useful, for example, in producing lithographic printing plates and photoresists.

In German Offenlegungsschrift No. 2,053,363, binders are described that result from the reaction between (a) polymers containing hydroxyl or amino groups and (b) at least one saturated alkyl-, alkoxy-, aryl- or aryloxysulfonyl isocyanate. In combination with diazonium salt polycondensation products or photopolymerizable compounds, however, these binders—for example, alkylsulfonylurethane resins—can only be developed in an aqueous-alkaline environment if they have relatively high acid numbers, which impairs the abrasion resistance of the cured layer.

German Offenlegungsschriften Nos. 2,053,364 and 3,036,077 describe photosensitive mixtures which contain, as the binders, reaction products of a polymer comprising hydroxyl groups and alkenylsulfonyl isocyanates. The printing plates produced with these mixtures show an insufficient ink receptivity, such that an unacceptably high number of waste sheets are produced at the beginning of printing. Moreover, the alkenylsulfonyl isocyanates required for the preparation of these binders can only be obtained at great expenditure and high cost, as is evident, for example, from German patent No. 1,297,601.

SUMMARY OF THE INVENTION

It is therefore an object of the present invention to provide starting materials for the preparation of photocrosslinkable polymers that are soluble in aqueous-alkaline solutions, have improved oleophilic properties and are more readily available than the above-mentioned polymers.

It is also an object of the present invention to provide a process for synthesizing intermediate compounds that are useful in the preparation of photocrosslinkable polymers.

It has been found unexpectedly that these objects are achieved in an outstanding manner by means of ethylenically unsaturated (thio)phosphinic acid isocyanates and isothiocyanates represented by formula I below. The binders which can be prepared from the compounds of the present invention are condensation products of these compounds and polymers containing hydroxyl or amino groups.

More specifically, there has been provided, in accordance with one aspect of the present invention, a compound represented by the formula

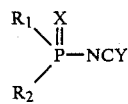   (I)

wherein

X and Y are the same or different, and each denotes oxygen or sulfur, $R_1$ is an ethylenically unsaturated aliphatic radical that contains from 2 to 6, particularly 2 to 4, and most preferably 2 to 3 carbon atoms, for example, a vinyl, allyl, methallyl or crotyl radical, and $R_2$ is a saturated aliphatic radical that contains from 1 to 6 carbon atoms, preferably 1 to 2 carbon atoms, or an unsubstituted or substituted aryl radical containing from 6 to 10 carbon atoms, in particular an unsubstituted or substituted phenyl radical.

In accordance with another aspect of the present invention, there has also been provided a process for preparing phosphinic acid and thiophosphinic acid isocyanates and isothiocyanates as described above, comprising the step of reacting a phosphinic or thiophosphinic acid chloride represented by the formula

   (II)

with an inorganic cyanate or thiocyanate, wherein X, $R_1$ and $R_2$ are as previously defined. In a preferred embodiment, the process comprises reacting the acid chloride with an alkali metal, ammonium or alkaline earth metal cyanate or thiocyanate.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The compounds of the present invention can be used to produce polymers with ethylenically unsaturated (thio)phosphinylurethane or (thio)phosphinylthiourethane, or (thio)phosphinylurea or (thio)phosphinylthiourea moieties in the lateral chains. Their use is described in concurrently-filed U.S. patent application Serial No. .... (87PAW200SAB).

Suitable substituents for $R_2$ in formula (I) include halogen, for example, fluorine, chlorine and bromine; alkyl; alkoxy containing from 1 to 6 carbon atoms; and aryl and aryloxy containing from 6 to 10 carbon atoms.

Among the preferred unsaturated (thio)phosphinic acid iso(thio)cyanates of the present invention are the following:

Allylmethylphosphinic acid isocyanate,
Allylmethylthiophosphinic acid isocyanate,
Allylmethylphosphinic acid isothiocyanate,
Allylmethylthiophosphinic acid isothiocyanate,
Crotylmethylphosphinic acid isocyanate,
β-Methallylmethylphosphinic acid isocyanate,
β-Methallylmethylphosphinic acid isothiocyanate,
Methylvinylphosphinic acid isocyanate,
Methylvinylthiophosphinic acid isocyanate,
Methylvinylphosphinic acid isothiocyanate,
Methylvinylthiophosphinic acid isothiocyanate,
Ethylvinylphosphinic acid isocyanate,
Butylvinylphosphinic acid isocyanate,
Phenylvinylphosphinic acid isocyanate, Phenylvinylthiophosphinic acid isocyanate,
Phenylvinylphosphinic acid isothiocyanate,
Phenylvinylthiophosphinic acid isothiocyanate.

The (thio)phosphinic acid derivatives of the present invention can be prepared with good yields from the corresponding (thio)phosphinic acid chlorides represented by the formula

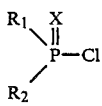
(II)

wherein $R_1$, $R_2$ and X have the meanings specified above, by reaction with inorganic cyanates or thiocyanates. Particularly suitable inorganic cyanates and thiocyanates in this context are alkali metal and alkaline earth metal salts, particularly the Na-, K- and Li-salts, but also ammonium salts.

The molar ratio between the (thio)phosphinic acid chlorides of formula (II) and the inorganic cyanate or thiocyanate salts preferably is about 1.

Suitable reaction media are aprotic, chemically non-reactive solvents. Illustrative of these are acetonitrile, aromatic hydrocarbons and chlorinated hydrocarbons. The preferred solvents are benzene, toluene and, in particular, acetonitrile.

In accordance with the present invention, the reaction mixture is stirred in the absence of moisture at temperatures of from 10° to 100° C., preferably from 20° to 60° C., until product formation has come to an end. Depending on the starting products used, this may take 4 hours or even up to 3 days.

Some of the (thio)phosphinic acid chlorides of formula (II) are known compounds and some are readily prepared via known processes. Methylvinylphosphinic acid chlorides and phenylvinylphosphinic acid chlorides can be prepared, for example, according to the following reaction scheme as described in German patent No. 2,357,678:

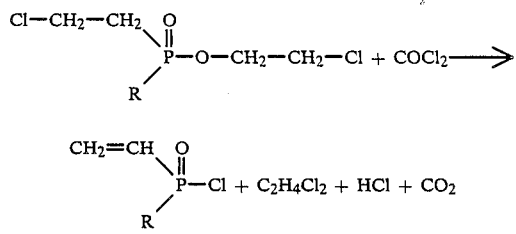

R = methyl, phenyl (Meth)allylphosphinic acid alkyl esters and crotylphosphinic acid alkyl esters which are obtainable by an Arbuzov-reaction, according to German patent No. 2,601,467, can be converted into the corresponding phosphinic acid chlorides by the use of phosgene.

It is also known that by thermal rearrangement of phosphonous acid alkyl esters, followed by reaction with phosphorus pentachloride, the corresponding allylphosphinic acid chlorides can be prepared in accordance with the following reaction scheme, as described by A. I. Pudovik et al., Z. Obsc. Chim. 37(3), 700 (1967):

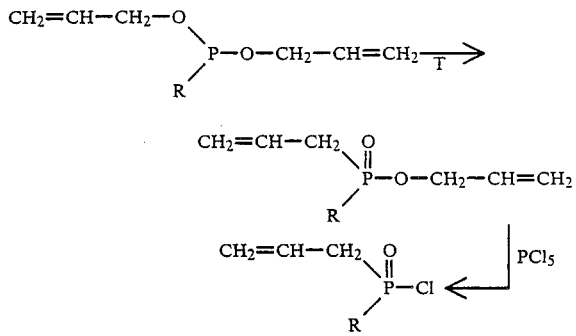

The present invention is explained in greater detail by reference to the following examples.

EXAMPLE 1

100 g (0.8 mol) of methylvinylphosphinic acid chloride were dissolved in 100 ml of acetonitrile. 52.2 g (0.8 mol) of sodium cyanate were added thereto in small amounts with vigorous stirring. The temperature was kept at a maximum of about 40° C. by cooling. The precipitate was filtered off by suction after stirring for 24 hours and washed thereafter with acetonitrile. The filtrate was concentrated in vacuo. The residue thus produced was distilled at a temperature of 58°-60° C. and at a pressure of 52.6 Pa. 88 g of methylvinylphosphinic acid isocyanate (83.5% of theory) were obtained.

$C_4H_6NO_2P$ (131): Calculated: 36.6% C, 4.6% H, 10.7% N, 23.7% P. Found: 35.9% C, 4.6% H, 10.3% N, 24.0% P.

EXAMPLE 2

50 g (0.35 mol) of methylvinylthiophosphinic acid chloride were dissolved in 80 ml of acetonitrile. 27.1 g (0.35 mol) of ammonium thiocyanate were added thereto in small amounts with vigorous stirring. The temperature was kept at about 30° C. by cooling slightly. After stirring for 3 days, the precipitate was filtered off by suction and then washed with acetonitrile. The filtrate was concentrated in vacuo. The residue thus produced was distilled at a temperature of 69°-70° C. and at a pressure of 1.33 Pa. 45 g of methylvinylthiophosphinic acid isothiocyanate (78% of theory) were obtained.

$C_4H_6NPS_2$ (163). Calculated: 29.5% C, 3.7% H, 8.6% N, 19.0% P, 39.3% S. Found: 29.5% C, 3.7% H, 8.4% N, 20.2% P, 39.4% S.

EXAMPLE 3

100 g (0.8 mol) of methylvinylphosphinic acid chloride were dissolved in 160 ml of acetonitrile. 61 g (0.8 mol) of ammonium thiocyanate were added thereto in small amounts during vigorous stirring. The temperature was kept at a maximum of 30° C. by cooling slightly. After 3 days of stirring, the precipitate was filtered off by suction and then washed with acetonitrile. The filtrate was concentrated in vacuo. The residue thus produced was distilled at a temperature of 70° C. and at a pressure of 6.7 Pa. 65 g of methylvinylphosphinic acid isothiocyanate (55.1% of theory) were obtained.

$C_4H_6NOPS$ (147). Calculated: 32.6% C, 4.1% H, 9.5% N, 21.2% P, 21.8% S. Found: 32.4% C, 4.1% H, 9.3% N, 21.2% P, 21.9% S.

EXAMPLE 4

(a) Allylmethylphosphinic acid chloride 120 g (0.81 mol) of ethylallylmethylphosphinate were dissolved in 100 ml of dichloromethane and phosgene was introduced with cooling at a temperature of 10°–15° C. in the course of 2.5 hours. Stirring was continued for another hour at 25° C. and then the readily volatile constituents were distilled off at reduced pressure. The residue was distilled at a temperature of 62°–66° C. and at a pressure of 130 Pa. 102 g of allylmethylphosphinic acid chloride (91% of theory) were obtained.

$C_4H_8ClOP$ (138). Calculated: 34.7% C, 5.8% H, 22.4% P. Found: 34.9% C, 5.8% H, 22.7% P.

(b) Allylmethylphosphinic acid isocyanate 166 g (1.2 mol) of allylmethylphosphinic acid chloride were dissolved in 300 ml of acetonitrile and heated with 78 g (1.2 mol) of sodium cyanate to 50°–55° C. with stirring. After 5.5 hours, the precipitate was filtered off by suction and washed with acetonitrile; the filtrate was concentrated and the residue distilled at a temperature of 78°–80° C. and at a pressure of 25 Pa. 123 g of allylmethylphosphinic acid isocyanate (71% of theory) were obtained.

$C_5H_8NO_2P$ (145). Calculated: 41.4% C, 5.6% H, 9.7% N, 21.4% P. Found: 41.6% C, 5.7% H, 9.5% N, 21.0% P.

EXAMPLE 5

(a) Crotylmethylphosphinic acid chloride 200 g (1.23 mol) of ethyl crotylmethylphosphinate were dissolved in 150 ml of dichloromethane, and phosgene was fed in while cooling at a temperature of 12°–15° C. over the course of 3.5 hours. Stirring was continued for another hour at 25° C., followed by distillation. 182 g of crotylmethylphosphinic acid chloride (97% of theory), with a boiling point of 83°–85° C. (260 Pa), were obtained.

$C_5H_{10}ClOP$ (153). Calculated: 39.4% C, 6.6% H, 20.3% P. Found: 39.9% C, 6.5% H, 20.1% P.

(b) Crotylmethylphosphinic acid isocyanate 170 g (1.1 mol) of crotylmethylphosphinic acid chloride were dissolved in 300 ml of acetonitrile and heated with 73 g (1.1 mol) of sodium cyanate to 55° C. with stirring. After 4.5 hours, the precipitate was filtered off by suction and washed with acetonitrile; the filtrate was concentrated and the residue distilled at a temperature of 76°–78° C. and at a pressure of 27 Pa. 123 g of crotylmethylphosphinic acid isocyanate (70% of theory) were obtained.

$C_6H_{10}NO_2P$ (159). Calculated: 45.3% C, 6.3% H, 8.8% N, 19.5% P. Found: 45.0% C, 6.2% H, 8.6% N, 19.4% P.

EXAMPLE 6

(a) β-methallylmethylphosphinic acid chloride 140 g (0.86 mol) of ethyl β-methallylmethylphosphinate were dissolved in 120 ml of dichloromethane, and phosgene was fed in at a temperature of 15°–20° C. in the course of 3 hours. Stirring was continued for another 2 hours at 25° C. and then distillation was carried out. 127 g of β-methallylmethylphosphinic acid chloride (97% of theory) with a boiling point of 66°–68° C. (27 Pa), were obtained.

$C_5H_{10}ClOP$ (153). Calculated: 39.4% C, 6.6% H, 20.3% P. Found: 39.8% C, 6.8% H, 20.6% P.

(b) β-methallylmethylphosphinic acid isocyanate 127 g (0.83 mol) of β-methallylmethylphosphinic acid chloride were dissolved in 200 ml of acetonitrile and heated together with 54 g (0.83 mol) of sodium cyanate during stirring at 50°–55° C. After 5 hours, the precipitate was filtered off by suction and washed with acetonitrile; the filtrate was concentrated and distilled at a temperature of 70°–75° C. and at a pressure of 13 Pa. of theory) were obtained.

$C_6H_{10}NO_2P$ (159). Calculated: 45.3% C, 6.3% H, 8.8% N, 19.5% P. Found: 45.2% C, 6.4% H, 8.6% N, 18.9% P.

EXAMPLE 7

106 g (0.57 mol) of phenylvinylphosphinic acid chloride were dissolved in 150 ml of acetonitrile and stirred with 38 g (0.59 mol) of sodium cyanate at a temperature of 30° C. After 23 hours, the precipitate was filtered off by suction and washed with acetonitrile; the filtrate was concentrated and the residue distilled at a temperature of 107°–110° C. and at a pressure of 33 Pa. 84 g of phenylvinylphosphinic acid isocyanate (77% of theory) were obtained.

$C_9H_8NO_2P$ (193). Calculated: 56.0% C, 4.2% H, 7.3% N, 16.0% P. Found: 54.9% C, 4.0% H, 7.1% N, 16.0% P.

EXAMPLE 8

83 g (0.55 mol) of β-methallylmethylphosphinic acid chloride were mixed in 200 ml of acetonitrile with 42 g (0.55 mol) of ammonium thiocyanate with slight cooling and then stirred at a temperature of about 30° C. After 3 days, the precipitate was filtered off by suction and washed with acetonitrile; the filtrate was concentrated and distilled. 72 g of β-methallylmethylphosphinic acid isothiocyanate (75% of theory) with a boiling point of 98°–100° C. (66 Pa), were obtained.

$C_6H_{10}NOPS$ (175). Calculated: 41.1% C, 5.8% H, 8.0% N, 17.7% P, 18.3% S. Found: 41.0% C, 5.6% H, 8.6% N, 17.4% P, 18.0% S.

EXAMPLE 9

61 g (0.33 mol) of phenylvinylphosphinic acid chloride in 150 ml of acetonitrile were mixed with 25 g (0.33 mol) of ammoniumthiocyanate while cooling slightly and then stirred for 40 hours at a temperature of 30° C.

The salt produced in this way was filtered off by suction and washed with acetonitrile; the filtrate was concentrated and distilled. 54 g of phenylvinylphosphinic acid isothiocyanate (80% of theory), with a boiling point of 130°–132° C. (66 Pa), were obtained.

$C_9H_8NOPS$ (209). Calculated: 51.7% C, 3.9% H, 6.7% N, 14.8% P, 15.3% S. Found: 51.8% C, 3.8% H, 7.2% N, 14.4% P, 15.8% S.

What is claimed is:

1. A compound represented by the formula

wherein

X and Y are the same or different, and each is oxygen or sulfur, $R_1$ is an ethylenically unsaturated aliphatic radical containing from 2 to 6 carbon atoms, and $R_2$ is a saturated aliphatic radical containing from 1 to 6 carbon atoms, or an aryl radical containing from 6 to 10 carbon atoms.

2. A compound as claimed in claim 1, wherein $R_1$ is an ethylenically unsaturated aliphatic radical containing from 2 to 4 carbon atoms.

3. A compound as claimed in claim 1, wherein $R_2$ is a saturated aliphatic radical containing 1 or 2 carbon atoms.

4. A compound as claimed in claim 1, wherein $R_2$ is an unsubstituted phenyl radial or a phenyl radical substituted with a substituent selected from the group consisting of a halogen, an alkyl group containing from 1 to 6 carbon atoms, an alkoxy group containing from 1 to 6 carbon atoms, an aryl group containing from 6 to 10 carbon atoms, and an aryloxy group containing from 6 to 10 carbon atoms.

5. A compound as claimed in claim 1, wherein
$R_1$ is a vinyl group,
$R_2$ is a methyl or ethyl radical or an unsubstituted phenyl radical, and
X and Y are oxygen atoms.

6. A process for the preparation of phosphinic acid and thiophosphinic acid isocyanates and isothiocyanates represented by the formula

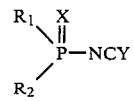  (I)

comprising the step of reacting an acid chloride consisting essentially of a phosphinic or thiophosphinic acid chloride represented by the formula

  (II)

with an inorganic cyanate or thiocyanate, wherein
X and Y are the same or different, and each is oxygen or sulfur,
$R_1$ is an ethylenically unsaturated aliphatic radical containing from 2 to 6 carbon atoms, and
$R_2$ is a saturated aliphatic radical containing 1 to 6 carbon atoms or an aryl radical containing from 6 to 10 carbon atoms.

7. A process as claimed in claim 6, wherein said acid chloride is reacted with an alkali metal, ammonium or alkaline earth metal cyanate or thiocyanate.

8. A process as claimed in claim 6, wherein said reaction is carried out at a temperature between about 10° and 100° C. and in the absence of moisture.

9. A process as claimed in claim 6, wherein said reaction is carried out in a solvent.

10. A process as claimed in claim 9, wherein said solvent is acetonitrile.

* * * * *